United States Patent [19]
Leisner et al.

[11] Patent Number: 6,135,986
[45] Date of Patent: Oct. 24, 2000

[54] OSTOMY APPLIANCE

[75] Inventors: Henrik Leisner, Gentofte; Eskil Hoijland Olsen, Klampenborg, both of Denmark

[73] Assignee: Coloplast A/S, Humlebaek, Denmark

[21] Appl. No.: 09/402,451

[22] PCT Filed: Apr. 7, 1998

[86] PCT No.: PCT/DK98/00143

§ 371 Date: Oct. 7, 1999

§ 102(e) Date: Oct. 7, 1999

[87] PCT Pub. No.: WO98/44880

PCT Pub. Date: Oct. 15, 1998

[30] Foreign Application Priority Data

| Apr. 8, 1997 | [DK] | Denmark | 0396/97 |
| Jun. 16, 1997 | [DK] | Denmark | 0699/97 |
| Jul. 4, 1997 | [DK] | Denmark | 0802/97 |

[51] Int. Cl.$^7$ .................................................. A61M 1/00
[52] U.S. Cl. .......................... 604/322; 604/324; 604/333
[58] Field of Search ..................................... 604/322, 332, 604/324, 333, 334, 337, 339, 342

[56] References Cited

U.S. PATENT DOCUMENTS

| 3,759,260 | 9/1973 | Nolan et al. ............................ 128/283 |
| 3,804,091 | 4/1974 | Nolan et al. ............................ 128/283 |
| 3,952,727 | 4/1976 | Nolan ..................................... 128/283 |
| 4,274,848 | 6/1981 | La Gro ................................... 55/387 |
| 4,411,659 | 10/1983 | Jensen et al. .......................... 604/332 |
| 4,490,145 | 12/1984 | Campbell ............................... 604/333 |
| 4,830,187 | 5/1989 | Keyes et al. .......................... 206/524.7 |
| 4,986,824 | 1/1991 | Steer et al. ............................ 604/333 |
| 5,167,650 | 12/1992 | Johnsen et al. ........................ 604/332 |
| 5,342,434 | 8/1994 | Wu ........................................ 96/13 |
| 5,348,546 | 9/1994 | Norton .................................. 604/333 |
| 5,549,587 | 8/1996 | Norton .................................. 604/333 |
| 5,690,623 | 11/1997 | Lenz et al. ............................ 604/333 |
| 5,693,035 | 12/1997 | Leise, Jr. et al. ...................... 604/333 |
| 6,015,399 | 1/2000 | Mracna et al. ......................... 604/332 |
| 6,050,982 | 4/2000 | Wheeler ................................ 604/332 |

FOREIGN PATENT DOCUMENTS

| 0 064 044 | 11/1982 | European Pat. Off. . |
| 0 089 110 | 9/1983 | European Pat. Off. . |
| 0 235 928 | 9/1987 | European Pat. Off. . |
| 0 443 728 | 8/1991 | European Pat. Off. . |
| 0 607 028 | 7/1994 | European Pat. Off. . |
| 75 25 408 | 4/1977 | Germany . |
| 1 571 382 | 7/1980 | United Kingdom . |
| 2 259 255 | 3/1993 | United Kingdom . |

*Primary Examiner*—Sharon Kennedy
*Assistant Examiner*—Kevin C. Simmons
*Attorney, Agent, or Firm*—Jacobson, Price, Holman & Stern, PLLC

[57] ABSTRACT

An ostomy appliance comprising a front wall and a rear wall of flexible material, the rear wall having an opening into the bag by which waste material can enter the bag and one of the walls has one or more vents through which gas may escape from the bag and having a filter covering said vent, said filter comprising an elongated, substantially flat filter body of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper end lower surfaces of the filter body, the arrangement being so that in use gas flows longitudinally through the filter from the inlet opening to the outlet opening, such gas flow being by a hydrophobic sheet, wherein the inlet opening is covered with a microporous oleophobic membrane and wherein a foam material is placed between the front wall and the rear wall and covering the inlet opening of the vent shows improved resistance against wetting and blocking of the filter.

12 Claims, 6 Drawing Sheets

OSTOMY APPLIANCE

This application is a 371 of PCT/OK98/00143 filed Apr. 7, 1998.

FIELD OF THE INVENTION

The present invention relates to an ostomy appliance comprising a deodorising filter, in particular ostomy bags, to a filter device and the use of a hydrophobic and oleophobic membrane for covering the inlet opening of deodorising filters especially for ostomy equipment in particular ostomy bags.

BACKGROUND OF THE INVENTION

In connection with surgery for a number of diseases in the gastrointestinal tract a consequence is, in many cases, that the patient is left with an abdominal stoma such as a colostomy, an ileostomy or an urostomy in the abdominal wall for the discharge of visceral contents. The discharge of viseral contents including intestinal gases cannot be regulated at will, and for that purpose the intestinal opening may be closed with a closure means, e.g. a tampon or a magnetic closure, or the patient will have to rely on an appliance to collect the material emerging from such opening in a bag which is later emptied and/or discarded at suitable times.

The discharge of flatus, measured in volume, may exceed the discharge of solid and liquid faecal matter by many hundred percent and therefore there is usually the need for the continuous or frequent venting of the intestine or the collecting bag. Normally the outflowing flatus is deodorised with a suitable filter. Commonly the active filter is powdered active carbon, which absorbs $H_2S$ being the principal component of the smell of flatus.

Various constructions of filters for ostomy appliances are known. In the state of the art, the filters are designed so as to obtain a high security of deodorisation of the flatus by insuring that there is no by-pass by which the flatus may circumvent the filter, and some measures have been discussed with respect to obtaining a better security against blocking of the inlet of the filter by solid discharged visceral content. When the inlet opening of the filter is blocked, the gas discharged into the ostomy appliance will lead to ballooning of the bag which is highly undesirable for several reasons. Ballooning will be embarrassing for the user as the bag will bulge and there is an increased risk of leakage which is unacceptable for the user. Another problem may arise when applying a fresh ostomy appliance as a vacuum in the bag may give a "pancaking" effect, i.e., the front wall and the rear wall stick together and are very difficult to separate which may hamper the discharge of visceral contents into the bag.

Examples of filters are described in U.S. Pat. Nos. 3,804,091, 3,952,727 and 3,759,260 wherein activated carbon particles are present in a filter body of matted fibres and wherein the filter body is arranged such that the flatus passes therethrough in various ways. However, it is a drawback of the filters known from these specifications that there is no firm surface connection between the filter body and the plastic, gas impermeable cover sheets therefor whereby a flow of gases may occur through the filter without passing through the filter body and hence without being deodorised. This for instance may take place as a result of bending or bowing the filter consequent e.g. upon the patient bending, which can cause small interspaces or channels to be formed between the filter body and one of the walls.

U.S. Pat. No. 4,490,145 discloses an ostomy pouch with a deodorising filter. The filter consists of a filter element affixed to the outside or inside of the pouch outer wall and comprising a polymeric film cover attached to the said pouch wall, and an insert of a gas deodorising material, e.g. of one of the kinds mentioned above. The pouch wall has an aperture providing entry to the filter element and the polymeric film cover has an aperture for venting the deodorised gas to the atmosphere. The two apertures are spaced from each other in order to let the intestinal gas pass through the length of the insert of deodorising material. U.S. Pat. No. 4,490,145 does not disclose a positive sealing connection between the film cover for the filter element and the insert of deodorising material but in a commercial ostomy pouch, "ConvaTex" made in accordance with this U.S. patent one surface of the deodorising material is sealed to the outer pouch wall whereas the opposite surface of the deodorising material is not sealed to the polymeric film cover; accordingly there is a space between the deodorising material and the cover through which gas can flow freely, especially in cases of bending of the filter. This means that the intestinal gas can pass directly across the thickness of the deodorising material, i.e. about 1 or 2 mm, and then through the space defined between such material and the polymeric film cover. Satisfactory deodorising cannot therefore be achieved.

A similar filter construction is disclosed in DE Utility Model No. 7525408 in which the filter element comprises a filter housing with apertures for the inlet and outlet of gases and containing an odour absorbing material. The latter may be connected with one side of the filter housing and the two apertures are spaced as far from each other as possible. Again, since only one side of the absorbing material is connected to a wall of the housing, the gas may pass between that wall and the absorbing material and may thus only be subjected to deodorising as a result of passing directly through the thickness of the absorbing material.

These drawbacks have been overcome by the filters described in GB 1,571,382 and EP 0089,110 in the name of Coloplast A/S, wherein a plastic wall has been glued or hot sealed to a filter body consisting of an open cell foam plastic impregnated with the activated carbon particles. These filters preferably are formed as circular discs of a thickness of 2–3 mm and a diameter of 25–30 mm and having an aperture in the centre of the filter material and in one of the walls arranged such that the flatus enters through the aperture in the wall and flows into the filter material through the edges of the aperture therein, and flows radially through the filter and leaves it through its cylindrical outer edge.

These filters function well and are particularly suitable for ostomy bags. They are adapted to yield a small gas resistance within the filter material and hence a low drop of pressure, and the same is true for the arrangements known from the US specifications discussed above. The purpose of the low drop of pressure is to ensure that the bag does not inflate and thereby become visible on the outside of the wearer's clothing, which should be avoided for obvious reasons. If, however, the drop of pressure becomes too low this can also create problems. Firstly it can occur that the entire volume of gas in the bag escapes so that the walls of the bag, consisting of a smooth plastic sheet material, stick together and also stick to the ostomy. This prevents faeces from the ostomy from falling to the bottom of the bag, and may also increase the risk of clogging the venting hole or holes in the wall of the bag. Sooner or later this can result in unacceptable bulging of the bag.

Secondly, a too high flow velocity through the filter may result in inefficient deodorising of the intestinal gases flowing out through the filter. The problem of avoiding a sudden fall of gas pressure in the interior of the pouch has also been taken into account in the above-mentioned U.S. Pat. No. 4,490,145 in which it is proposed, in order to keep the gas deodorising material dry and control the rate at which gas can pass from the pouch into the filtering element, to cover the inlet and/or outlet aperture by a barrier layer of a gas permeable, liquid impermeable material. However, such barrier layers will not only create a certain distension of the pouch itself, but also tend to cause distension between the insert of gas deodorising material and the surface thereof not sealed to the pouch wall and hence promote the above-mentioned tendency for the gas to travel through only the thickness of the insert and not along its length. This in turn will promote a fall of gas pressure in the interior of the pouch.

European patent No. 0 235 928 discloses a filter for ostomy bags and the like in which a higher drop of pressure occurs therein than in known filters, but wherein the drop of pressure is not so great as to cause over inflation of the bag offering a solution how to overcome the drawbacks of known arrangements mentioned above and to provide venting for ostomy bags and the like. The drop of pressure being higher than in known filters ensures that the bag is maintained inflated to a suitable degree by the intestinal gas which flows in more or less continuously so that wall of the bag opposite the filter does not stick to the opposite wall giving rise to an build up of pressure which will be unmistakable on the outside of the patient's clothing, which for psychological reasons clearly should be avoided but not be so big such that high inflation of the bag occurs in any case.

European Patent No. 0 235 928 further discloses that a filter may be rendered suitable for use with ileostomy equipment when the filter wall adapted to face the source of intestinal gas is covered by a layer of sheet material, preferably plastic sheet material connected to the filter walls and inside the periphery of this connection, provided with openings for the passage of intestinal gas. Conveniently these openings, which may for instance be slits of a width of 0.5–1 mm and a length of a few millimeters, may be situated outside the peripheral edge of the filter body. However, such slits may open if the pressure is high giving free flow of gas and liquid through the layer of sheet material. In the alternative, it is proposed to provide the filter housing on the surface adapted to face the source of intestinal gas with a layer of liquid-absorbing material. The area of the absorbent material is conveniently the same as the area of the filter body or somewhat larger but the positioning on the wall in question should be such that the absorbent material does not cover the inlet opening for intestinal gas to be deodorised since saturation of the liquid-absorbing material with liquid might prevent the passage of the intestinal gas. Furthermore, it is proposed to render the filter particularly efficient for ileostomy equipment by providing it both with a covering sheet and an absorbent layer of material.

EP patent No. 0 443 728 B1 discloses a bag for receiving discharge from the human body comprising a filter and an intervening membrane covering the inlet opening of the filter, said intervening membrane being gas permeable but not liquid permeable. It is mentioned that the membrane may comprise a polyester film bonded to a PTFE film and that such membrane showed no leakage of water. There is no indication of security against leaking when exposed for discharge from an ileostomy or liquids from a colostomy.

British patent No. 1 571 382 discloses collection bag having a venting device situated between the skin of the patient and the collection bag surrounding the inlet opening of the collection bag which venting device may have an inner ring of a gas-permeable hydrophobic material or of an open-celled hydrophobic foam plastics material. This reference does not offer a solution to the problems mentioned above.

GB 2 259 255 discloses a medico-surgical collection bag for body waste products comprising a front wall and a rear wall of flexible material. The rear wall has an opening into the bag by which waste material can enter the bag and one of the walls has vents and a seal for the vent such that when the seal is open, the front wall can be pulled away from the rear wall and then air is drawn through the vents and is trapped within the bag. The air trapped in the bag when closing the vent keeps the front wall away from the rear wall in the region of the inlet opening. This measure, however, only provides a solution to the second problem, the "pancaking", and is only effective when the opening of the vent is closed and does not prevent blocking of the inlet of the filter by solid discharged visceral content of the bag.

U.S. Pat. No. 5,549,587 discloses an ostomy bag having a liquid-gas separating device made of an absorbent material to collect liquids. Such a solution may overcome the problem of "pancaking". However, there is not a restricted access to the inlet opening of the filter and there is no teaching of a direct protection of the inlet opening of the filter against clogging.

U.S. Pat. No. 5,342,434 discloses a gas permeable coated porous membrane having enhanced oleophobic and hydrophobic properties. The membrane may be a PTFE membrane coated with a diisocyanate coating and the membranes are stated to be useful in waterproof, breathable fabrics and gas vents or filters that protect electronic equipment used in or near automotive engines. Other useful applications are stated to be medical devices where venting filters are needed and in industrial filtration where venting filters are needed, where oil mists are present. It is even stated that the coated products are useful as filters in medical vents where oil or fatty substances in parental drip bottles can clog gas vents. However, this reference is silent with respect to safety against wetting of filters for ostomy appliances by the visceral contents of an ostomy collection bag which contents has a very complex composition of biologically active compounds fro the digestive system.

U.S. Pat. No. 4,490,145 discloses an ostomy appliance comprising a front wall and a rear wall of flexible material, the rear wall having an opening into the bag by which waste material can enter the bag and one of the walls has one or more vents through which gas may escape from the bag and having a filter covering said vent, said filter comprising an elongated, substantially flat filter body of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper and lower surfaces of the filter body, the arrangement being so that in use gas flows longitudinally through the filter from the inlet opening to the outlet opening, such gas flow being confined to said filter element, wherein the inlet opening is covered by a water impermeable sheet.

U.S. Pat. No. 5,342,434 discloses gas permeable materials being hydrophobic and oleophobic and the use of such materials for thereof in filters of medical vents where oil or fatty substances in parental drip bottles can clog gas vents. Furthermore, the use as a vent to vent air, water vapour, or other gases from an interior area, but yet due to the coating prevents oils from clogging the vents and to filter particulate impurities from an air stream in environments where presence of oils may tend to clog the pores of the material.

Thus, no method for avoiding wetting of the filter material caused by humidity or other liquid constituents of the visceral contents of an ostomy collection bag and at the same time preventing clogging of the filter has yet been proposed. Such liquids are not held back by hydrophobic surfaces and will cause wetting of the filter material which may lead to a blocking of the filter causing a build up of an undesirable pressure in the bag as mentioned above and may also lead to leakage and break-through of liquid through the filter which may cause a wetting of the patient's clothing and also to the liberation of unpleasant odours. Furthermore, there is still a need of measures for effectively preventing blocking of the inlet opening of filters of ostomy appliances and "pancaking" of ostomy appliances.

It has surprisingly been found that it is possible to reduce the risk of wetting of the filter material and at the same time to reduce the risk of blocking of the inlet opening of filters of ostomy appliances. Furthermore, it has been found that it may also be possible to overcome the problem of "pancaking" at the same time and to minimise the risk of flatus bypassing the filter.

It has surprisingly been found that the above drawbacks can be avoided if the inlet opening of the filter is covered with a microporous oleophobic membrane and a prefilter.

BRIEF DESCRIPTION OF THE INVENTION

The invention relates to an ostomy equipment having a deodorising filter especially ostomy bags, of the type wherein the active filter material is a substantially flat, porous, elongate filter body of a material such as activated carbon textile material or non-woven fibres or foamed plastics impregnated with highly activated carbon.

Furthermore, the invention relates to a deodorising filter device especially apt for an ostomy appliance and the use of a hydrophobic and oleophobic membrane for covering the inlet opening of deodorising filters especially for ostomy equipment in particular ostomy bags.

BRIEF DESCRIPTION OF THE DRAWINGS

The invention is disclosed more in detail with reference to the drawings in which.

DETAILED DESCRIPTION OF THE INVENTION

The invention relates in a first aspect to an ostomy appliance comprising a front wall and a rear wall of flexible material, the rear wall having an opening into the bag by which waste material can enter the bag and one of the walls has one or more vents (3) through which gas may escape from the bag and having a filter covering said vent, said filter comprising an elongated, substantially flat filter body (10) of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper and lower surfaces of the filter body, the arrangement being so that in use gas flows longitudinally through the filter from the inlet opening to the outlet opening, such gas flow being confined to said filter element, wherein the inlet opening is covered by a water impermeable sheet, said ostomy appliance being characterised in that the filter material is interposed between gas and liquid impervious walls (11,12) forming a filter device (4) having gas inlet (15) and outlet (16) openings in communication with the filter wherein the inlet opening (15) is covered with a microporous hydrophobic and oleophobic membrane (17), that the outlet opening (16) of the filter device (4) and the vent (3) are aligned, that said membrane (17) is covered with a wall (18) defining a space for placing a foam material (5) between the front wall and the rear wall and covering the inlet opening of the vent and that the wall (18) has one or more inlet openings (7,20) leading into the space comprising the foam material.

The ostomy appliance according to the invention reduces the risk of blocking of the inlet of the filter and of wetting and break-through of liquid through the filter and "pancaking" of ostomy appliances. At the same time, a rigidity is imparted to the ostomy appliance giving an improved performance as the tendency of the top of the appliance to fold over and optionally block the inlet opening of a vent is prevented. Thus, the appliance is rendered very suitable for use for all ostomy purposes, colostomy, ileostomy.

In one embodiment of the ostomy appliance, the oleophobic membrane covering the filter is sealed to the walls of the ostomy appliance around the inlet opening of the deodorising filter. This embodiment is especially suitable if the filter is placed on the outside of the appliance.

In another aspect, the invention relates to a deodorising filter device (9) especially apt for an ostomy appliance or the like, the filter comprising an elongated, substantially flat filter (10) body of a porous filter material interposed between gas and liquid impervious first and second walls which are sealed to the body along its longitudinal side edges; gas inlet and outlet openings being provided in communication with the filter material adjacent to its respective longitudinal end regions in the first and second wall, respectively, wherein both of the gas and liquid impervious walls are sealed to the upper and lower surfaces of the filter body, the arrangement being such that in use gas flows longitudinally through the filter from the inlet opening to the outlet opening, such gas flow being confined to said filter element wherein the inlet opening is covered by a water impermeable sheet, said filter device being characterised in that the filter is imposed between gas and liquid impervious walls (11,12) forming a filter device (4) having gas inlet (15) and outlet (16) openings in communication with the filter, that the inlet opening (15) is covered with a microporous hydrophobic and oleophobic membrane (17), that said membrane (17) is covered with a third wall (6,18) secured to the first wall (11) having the inlet opening (15) and defining a space wherein a foam material (5) is placed between the third wall and the first wall and covering the inlet opening of the vent and that the third wall has one or more inlet openings (7,20) leading to the space comprising the foam material.

The filter device preferably has inlet openings at both ends in order to ensure free entrance of gas into the filter device, through the inlet opening, through the filter and eventually free exit of deodorised gas through the outlet opening of the filter and the bag. The filter package may be secured to one of the walls of the ostomy appliance by welding. Preferably, the outlet opening is only formed after securing the filter package to the wall of the ostomy appliance by punching a hole through the wall of the appliance and the backing sheet of the filter into the filter material using a hot needle or the like. Thus, a perfect alignment of the outlet openings of the filter package and of the ostomy appliance is ensured.

A filter device according to the invention also overcomes the disadvantages of the appliances of the state of the art with respect to blocking and "pancaking" without having a thickness bothering the ostomate.

The walls of the filter device are preferably of a size leaving an outer rim or flange being apt for securing the filter device to an ostomy appliance. The device may be secured and sealed by any suitable means, e.g. by welding or gluing.

The filter device may be secured to a wall of an ostomy appliance at any suitable step in a conventional process for preparing ostomy appliances and it is within the scope of the invention to produce the inlet hole after securing the filter device, e.g. by cutting or punching a hole through the wall of the appliance and the filter device.

Such a filter device combines the advantages of the device disclosed in EP Patent No. 0 235 928 B1 with an improved safety against leaking of liquid from the inside of an ostomy or ileostomy appliance through the filter.

Preferably, the thickness of the filter body is 0.25 to 3.0 mm and the distance between the inlet opening and the outlet opening, as measured between the edges thereof which are closest together, is at least 10 mm, more preferred up to 30 mm or even more, depending of the pressure drop over the filter.

The two walls mentioned, which together form a filter housing may be of any plastic sheet material normally used in connection with ostomy equipment, in particular ostomy bags; the only condition is that the material should be compatible with the plastic material of which the ostomy equipment in question is made, at least in the region of the side thereof to which the filter is preferably located. In the case of ostomy bags the filter is preferably placed on the inside of the bag. When used in, connection with tampons as described in e.g., EP Patent No. 0 188 376, see especially FIGS. 5–7, it may be placed on the side of a cover sheet which faces the body of the wearer or on the side thereof which faces away from the body. When a filter device in accordance with the invention is placed on the side of a bag or cover sheet which in use faces away from the body, there are openings in the bag or sheet permitting the intestinal gas to flow to the inlet opening of the filter housing, and if the filter is placed on the inner side of the bag or cover sheet, there are preferably openings therein which communicate with the outlet opening of the filter housing. Mounting on an ostomy bag or other ostomy equipment normally takes place by heat sealing, gluing or by similar means.

The filter body may be formed in various ways and may advantageously consist of a compressed foamed plastic impregnated with (i.e. containing in its pores) a highly activated carbon. This may for instance be activated by a metal salt, notably a heavy metal salt. A suitable material of this kind is known under the trade name "LR96 Charcoal impregnated Foam", supplied by Bondina Industrial Greetland, Halifax, England. In another embodiment the filter body consists of an activated carbon textile material. Such carbon textile material is known from e.g. the paper by Richard B. Macnair and Gilbert Arons, "Absorptive Textile Systems Containing Activated Carbon Fibres" in P.N. Cherimisonoff and F. Elabsh, "Carbon Absorption Handbook" (1978), Chapter 22.

The materials are known commercially under various names, e.g., "Charcoal Cloth", "C-Tec activated Carbon Textile" and "RK Carbon fibres". They are made from fibres, yarn or woven or knitted textile articles by the pyrolysis into carbon in an inert atmosphere at a temperature up to 500° C., followed by activation (formation of pores and surface area) at a higher temperature, about 1000° C., in an oxidating atmosphere, e.g. carbon dioxide or superheated steam. Such materials possess a high surface area, of the order 250–1200 $m^2/g$ because of the formation of small pores. The fibres, yarns or textiles subjected to the pyrolysis according to current information should be of a polymer which carbonises without melting.

In a leaflet from Siebe Gorman, "C-Tex Activated Carbon Textile" it is stated that such materials have been used for filters for colostomy bags but details are not given.

The entire surface area of the filter material is preferably sealed to the walls, e.g. by gluing, heat sealing or other suitable means, and the same is true for its edges except adjacent the longitudinal ends of the filter body. The sealing may cause difficulties in some cases but e.g. carbon textile material may be surface fixed by a so-called hot melt film of a non-woven textile of, e.g., nylon which may thereafter be easily hot-welded to the plastic walls. A suitable material is "Wonder-Web" from Bondina, Great Britain.

The regions of the filter body for the inlet of intestinal gas and outlet of deodorised intestinal gas are in practice most conveniently the longitudinal end edges of the filter body but may alternatively be e.g. surface area regions closely bordering the end edges.

As mentioned above the filter should provide a drop of pressure which is bigger than the drop of pressure in known filters but not so high as to not cause undesirable high inflation of the bag. By suitable relative dimensioning of the thickness and possibly the width of the filter and distance between the openings it is expedient in practice that the pressure drop through the filter corresponds to at least 30 and at most 175 mm water column at a flow rate of 50 ml gas or gas mixture per minute when the filter body is of the kind comprising compressed foam plastic impregnated with carbon highly activated by heavy metal salts. In the case where the filter body is formed of a carbon textile material, the drop of pressure is typically somewhat higher, e.g. 75–250 mm water column at a flow of the gas or gas mixture of 25 ml/minute.

The arrangement in practice of the filter body and the walls may vary. In one advantageous embodiment the inlet opening for intestinal gas and the outlet opening for deodorised intestinal gas are situated in the walls adjacent or directly outside and opposite the end edges of the filter body, the length of the filter body being at least 15 mm, preferably at least 20 mm and expediently 25–50 mm. The intestinal gas thereby enters the filter through one end edge and after deodorising escapes through the other, and if the two openings are substantially identical and extend substantially across the entire end edges of the filter body, it will not be the width and the thickness of the openings that determine the active cross sectional area of the filter and then the openings are an unimportant factor for determining the pressure drop through the filter. With a width of the filter body of at least about 5 mm, a length of 30 mm and a thickness of about 1.5 mm in the case of impregnated foam plastic and about 0.5 mm in the case of a carbon textile material there is, in a preferred embodiment, obtained a drop of pressure in the above-mentioned desirable ranges.

The hydrophobic sheet and the oleophobic membrane may according to the invention separate units or may be constitute a laminate of two layers having the respective properties. One layer may e.g. be made from glass fibres being treated to show hydrophobic or oleophobic properties. However, it is preferred according to the invention that the hydrophobic sheet covering the inlet opening is also oleophobic. This preferred embodiment shows the best security against clotting as the constituent being able to pass the first of two layers will not accumulate in a space between two layers.

The oleophobic membrane is preferably sealed to a wall of the filter device giving a more simple application having a better security against leakage. An optional wall or layer will preferably surround the deodorising filter inlet opening to avoid breaking the wall of the filter device when heat sealing the membrane to the wall.

In a preferred embodiment, the oleophobic sheet covering the inlet opening comprises a layer of a non-woven material and a layer of a PTFE-material treated to provide it with oleophobic properties. Such a sheet combines the hydrophobic properties and the oleophobic properties with a sufficient physical strength and good properties for heat sealing, heat welding or gluing.

In the present context, the term "oleophobic" is used to designate a material having surface properties repelling liquids having a lower surface tension than pure water (about 70 mN/m), e.g. a surface tension of less than 70 mN/m, preferably 15–70 mN/m.

The foam material placed between the front wall and the rear wall and covering the inlet opening of the vent is preferably in the form of a non-absorbing distance piece.

Foam materials suitable for use as a distance piece for ostomy appliances are open cell foam materials being resistant to the aggressive environment of the visceral contents discharged from the ostomy and not giving rise to liberation of noxious materials. An example of a suitable material is an open-cell polyether foam or an open-cell polyurethane foam.

The foam material preferably has a thickness of from 1 to 10 mm, more preferred from 3 to 5 mm ensuring that the ostomy appliance comprising the foam material overcomes the disadvantages of the appliances of the state of the art with respect to blocking and "pancaking" without having a thickness bothering the ostomate.

It is especially preferred if the foam material is in itself hydrophobic or rendered hydrophobic as the risk of blocking is reduced due to a repellent action against the visceral contents discharged from the ostomy. It is especially advantageous if a foam material is rendered hydrophobic or more hydrophobic by treatment with a silicone compound as silicones compounds show an anti-foaming effect.

In a preferred embodiment of the invention, the foam material is also rendered oleophobic further improving the resistance against blocking of the filter.

The ostomy appliance according to the invention may be an open or a closed appliance suitable for use in connection with a colostomy, an ileostomy or a urostomy. It may be a one-piece appliance or a two-piece appliance comprising a body side ostomy member and a separate collection bag. A separate collection bag may be attached to the body side member in any convenient manner, e.g. via a coupling ring or by a flange covered with an adhesive.

An ostomy appliance according to the invention may be made from materials conventionally used for the preparation of ostomy appliances in a manner known per se in the field.

In accordance with another preferred embodiment of the invention, a covering sheet is placed between the distance piece and the opening into the bag by which waste material can enter the bag in order to prevent the waste material from moving directly into the porous material for improving the security against blocking.

The covering sheet is preferably secured to the wall of the appliance around the vent opening in a manner defining a space comprising the distance piece improving the security against blocking.

In a further aspect the invention relates to a distance piece for insertion into an ostomy appliance comprising a front wall and a rear wall of flexible material, the rear wall having an opening into the bag by which waste material can enter the bag and one of the walls having one or more vents through which gas may escape from the bag, said distance piece being adapted to fit between the front wall and the rear wall and to cover the inlet opening of the vent.

A distance piece according to the invention may simply be inserted during the manufacture of the ostomy appliance and may optionally be secured to the front wall or the rear wall of the appliance or to both walls, e.g. by welding.

In a still further aspect, the invention relates to the use of a piece of a foam material as a distance piece for insertion into an ostomy appliance comprising a front wall and a rear wall of flexible material, the rear wall having an opening into the bag by which waste material can enter the bag and one of the walls having one or more vents through which gas may escape from the bag, said distance piece being adapted to fit between the front wall and the rear wall and cover the inlet opening of the vent.

In a further preferred embodiment of the invention, the filter body has a curved conformation giving a better adaptation to the surface of the body and enabling the use of a filter having a greater length. Such filters having a "banana form" offer a better capacity for absorption of $H_2S$ and reduce the risk of formation of small interspaces or channels being formed between the filter body and one of the walls as a result of bending or twisting the filter, e.g. when the patient bends over as such channels most often are rectilinear.

In still a further embodiment of the invention the ostomy appliance is in the form of a one-piece appliance having an adhesive plate for securing the same to the abdomen of an ostomate which adhesive plate is not circular but has a circular lower part and a non-circular upper part being more "flat". The upper, non-circular part of the adhesive plate may have an elongated contour and is preferably oval or elliptical. This embodiment renders it possible to place the adhesive plate more closely to the top of the bag which reduces the risk of a fold over of the top part of the ostomy appliance and thus the risk of blocking of the vent and furthermore increases the capacity of the bag as the inlet hole may be placed nearer the top of the bag.

Preferably, this embodiment also comprises a cutting guide having the same general non-circular shape rendering it more suitable for adaptation to non-circular ostomies. In a further embodiment, the inlet hole of the appliance is non-circular, preferably oval, rendering the bag more easy to adapt to non-circular ostomies and especially a so-called "loop ostomy" as it may, in many cases, not be necessary to cut at all.

In a further aspect, the invention relates to the use of a hydrophobic and oleophobic membrane for covering the inlet opening of deodorising filters for ostomy equipment, in particular for ostomy bags.

DETAILED DESCRIPTION OF THE DRAWINGS

Figure 1:
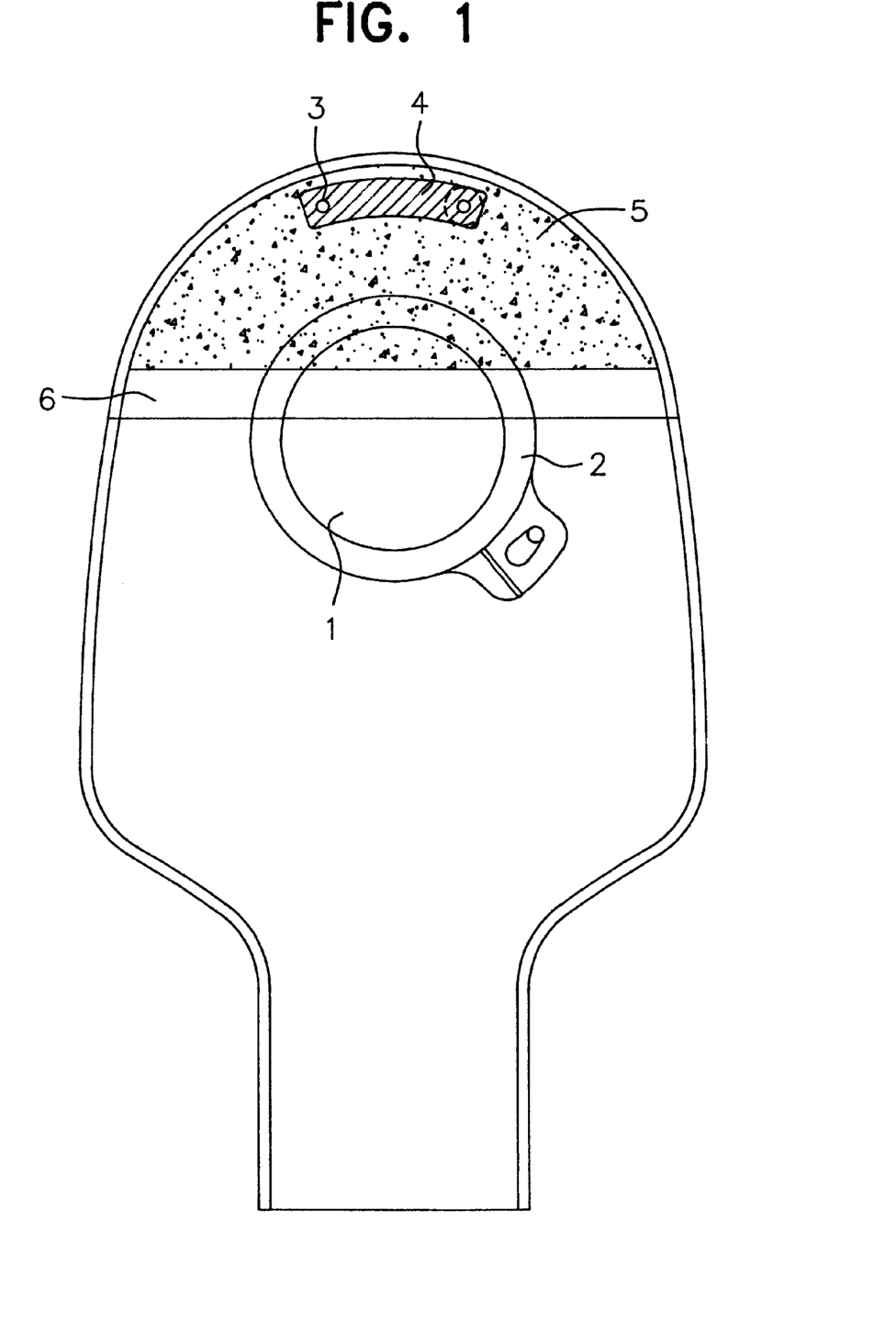
FIG. 1 shows a first embodiment of an ostomy appliance according to the invention.

The invention is disclosed more in detail with reference to the drawings in which: FIG. 1 shows an embodiment of an open ostomy appliance of the invention comprising a front wall and a rear wall of a flexible material, said rear wall having an opening 1 into the bag by which waste material can enter the bag. The opening has a coupling ring 2 for engaging with a corresponding coupling ring placed on a body side member. Furthermore, the appliance has a vent opening 3 on the front wall, said vent opening being covered of a filter device 4 wherein the inlet of the filter is covered by a microporous hydrophobic and oleophobic membrane covered with a protecting layer. At the inner side of the front wall is a protecting layer in the form of a piece 5 of a foam material. The appliance also has a sheet 6 situated between the inlet opening and the foam material.

The hydrophobic and oleophobic membrane reduces the risk of wetting of the filter material and the foam material improves the security against blocking as the direct path form the inlet opening of the ostomy appliance and the inlet opening of the filter is interrupted. Material entering the bag is guided away from the filter device by the sheet, and furthermore the passage to the inlet of the filter is filled with a foam material having a large inlet area and thus being less susceptible to blocking than the narrow inlet opening of the filter itself.

Figure 2:
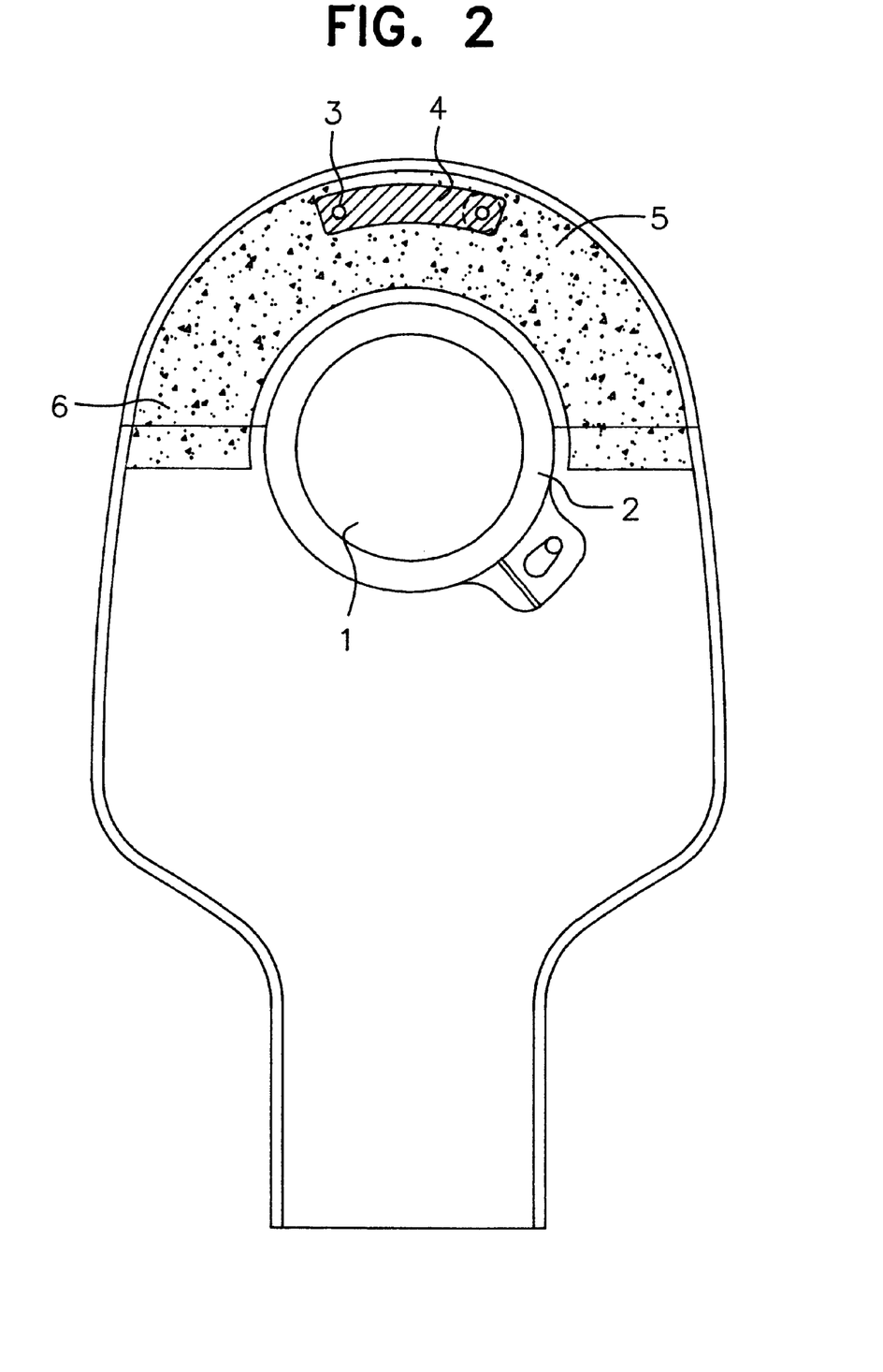
FIG. 2 shows a second embodiment of an ostomy appliance according to the invention.

FIG. 2 shows another embodiment of an appliance according to the invention in which the reference numerals 1–6 have the same meanings as in FIG. 1. The foam material 5 and the sheet 6 are in this embodiment not covering the inlet opening of the bag. The sheet may be secured to the rear wall or the front wall for reducing the risk of blocking, e.g. by gluing or preferably by welding.

The sheet may be of any suitable material, preferably of a material normally used for the preparation of ostomy appliances.

The appliances shown in FIGS. 1 and 2 are open and mostly for use in connection with ileostomies normally secreting a relatively liquid material.

Figure 3:
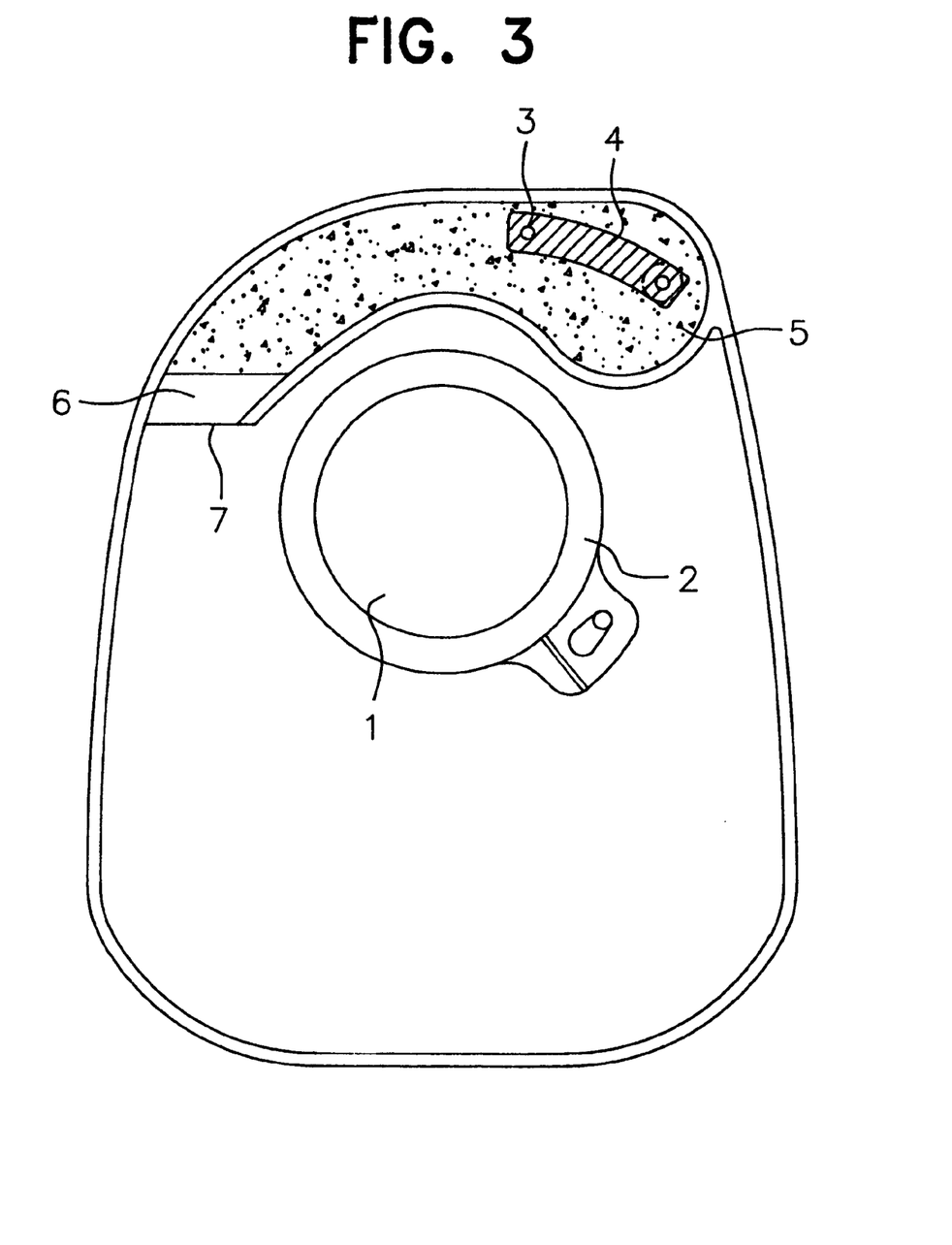
FIG. 3 shows a third embodiment of an ostomy appliance according to the invention.

The embodiment of the invention shown in FIG. 3 is a closed ostomy appliance. The reference numerals 1–6 have the same meanings as in FIG. 1. In this embodiment, the filter is secured to the rear wall and the sheet is relatively short and is secured to the rear wall along the major part of the lower edge. This leaves an opening 7 leading into a space or compartment 8 comprising the foam material.

In this embodiment the risk of blocking is reduced considerably as closed bags are mostly used for colostomies normally secreting relatively solid material.

Figure 4:
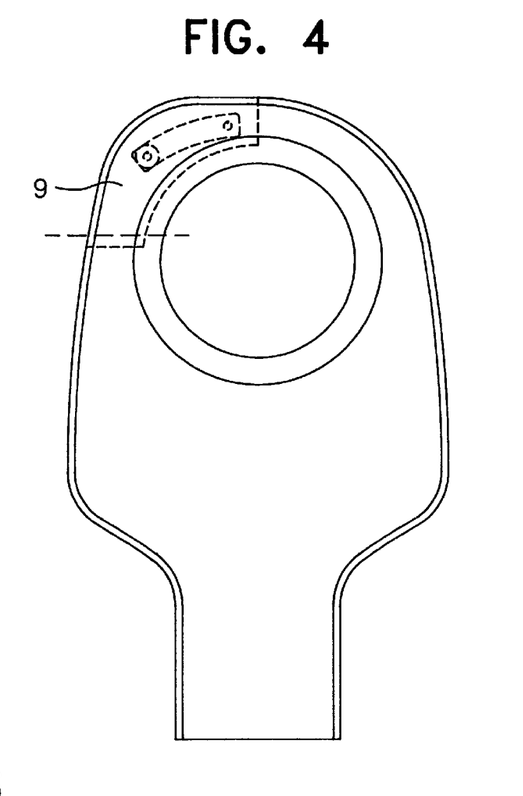
FIG. 4 shows a further embodiment of an ostomy appliance of the invention.
Figure 5:
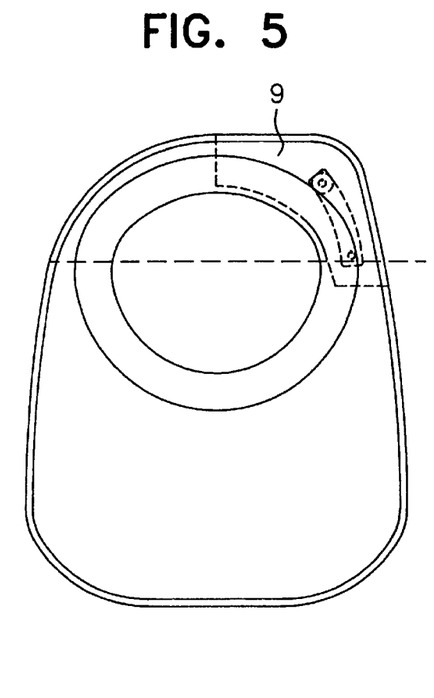
FIG. 5 shows another embodiment of an ostomy appliance of the invention.

FIGS. 4–5 show further embodiments of ostomy appliances according to the present invention for use on the left and right side of the abdomen, respectively, seen from the proximal side. Thus, FIG. 4 shows an open ostomy appliance of the invention having a filter device 9 of the invention secured to the wall of the appliance. In this embodiment the adhesive plate is not circular but has a circular lower part and a non-circular oval or elliptic form upper part. FIG. 5 shows a closed ostomy appliance of the invention having a filter device 9 of the invention secured to the wall of the appliance. The filter device may be secured to the front wall or the rear wall as desired and is preferably secured to the wall by welding in a manner known per se.

Figure 6:
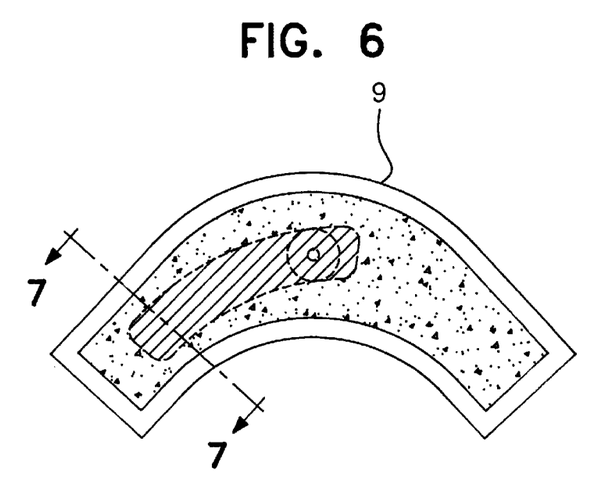
FIG. 6 shows an embodiment of a filter device of the invention.
Figure 7:
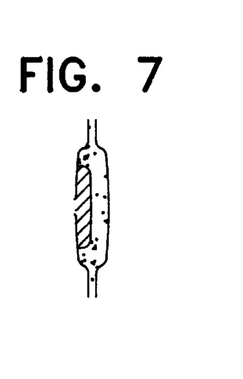
FIG. 7 shows a section along the line 7—7 of the embodiment of FIG. 6.

FIG. 6 shows a filter device according to the invention comprising a front sheet and a backing sheet of impervious material. The filter is secured to one of the sheets being welded together along two edges leaving the ends open. As appears from FIG. 7, the space in the package is filled with a foam material. The front sheet and the backing sheet may be of any suitable material, preferably a material normally used for the preparation of ostomy appliances or a material which may be glued or welded to such materials.

Figure 8:
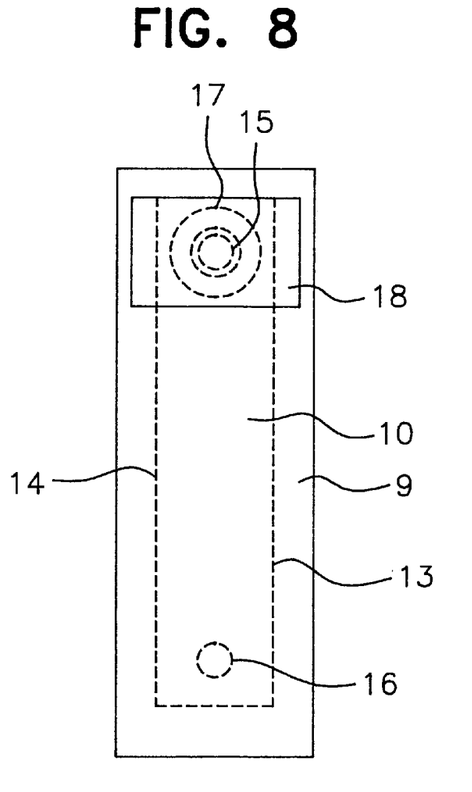
FIG. 8 shows an embodiment of a filter device according to the invention seen from the inlet side.
Figure 9:
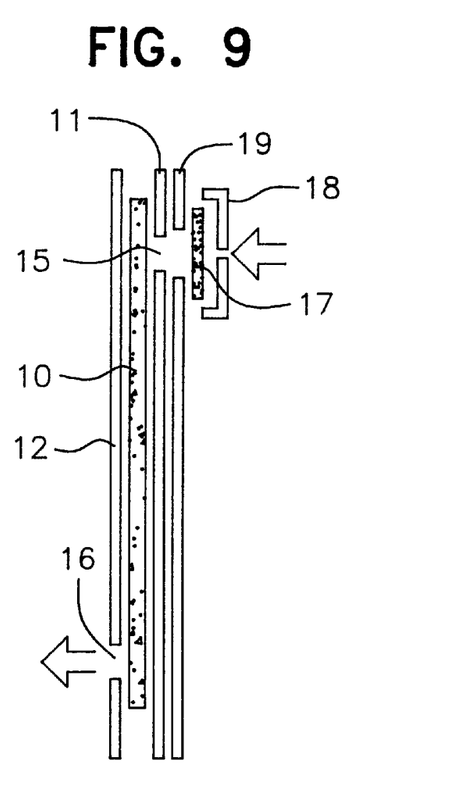
FIG. 9 shows an exploded sectional view of the embodiment of FIG. 8.

Reference is made to FIGS. 8 and 9 showing the principle of an embodiment of a filter device 9 according to the invention for an ostomy appliance or the like, the filter device comprising an elongated, substantially flat filter body 10 of a porous filter material interposed between gas and liquid impervious walls 11,12 which are sealed to the body along its longitudinal side edges 13,14; gas inlet 15 and outlet 16 openings being provided in communication with the filter material adjacent to its respective longitudinal end regions, wherein both of the gas and liquid impervious walls are sealed to the upper and lower surfaces of the filter body, the arrangement being such that in use gas flows longitudinally through the filter from the inlet opening to the outlet opening, such gas flow being confined to said filter element and wherein the inlet opening is covered by a hydrophobic sheet 17, which sheet is a microporous oleophobic membrane. The microporous oleophobic membrane is covered with a wall 18 defining a space for placing a foam material to avoid physical blocking which wall is secured to the wall 11 of the filter or to an optional layer 19 of the ostomy appliance. The wall 18 may be made from a suitable plastic material such as a polyolefin, e.g., PE, and may be secured above and below the inlet of the filter leaving the sides open or may be secured around the opening and have inlet openings allowing gas to enter from the ostomy appliance.

The optional layer 19 offers a simplification during the production of the filter device as the membrane 17 may be secured to the layer 19 before the final assembling of the filter. The layer 19 may stretch beyond the limits of the filter and be secured directly to the wall of the ostomy appliance.

Figure 10:
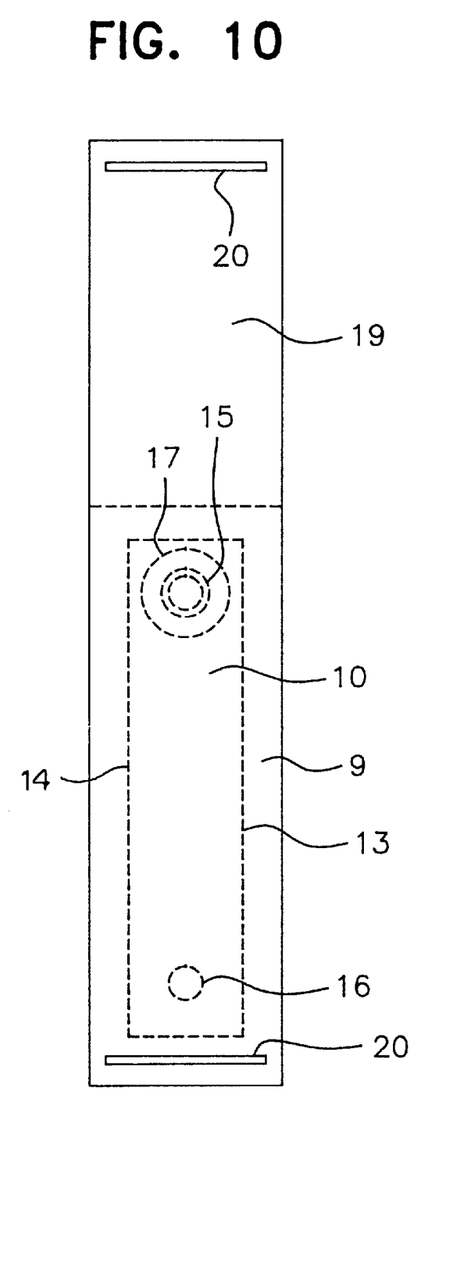
FIG. 10 shows another embodiment of a filter device according to the invention seen from the inlet side.
Figure 11:
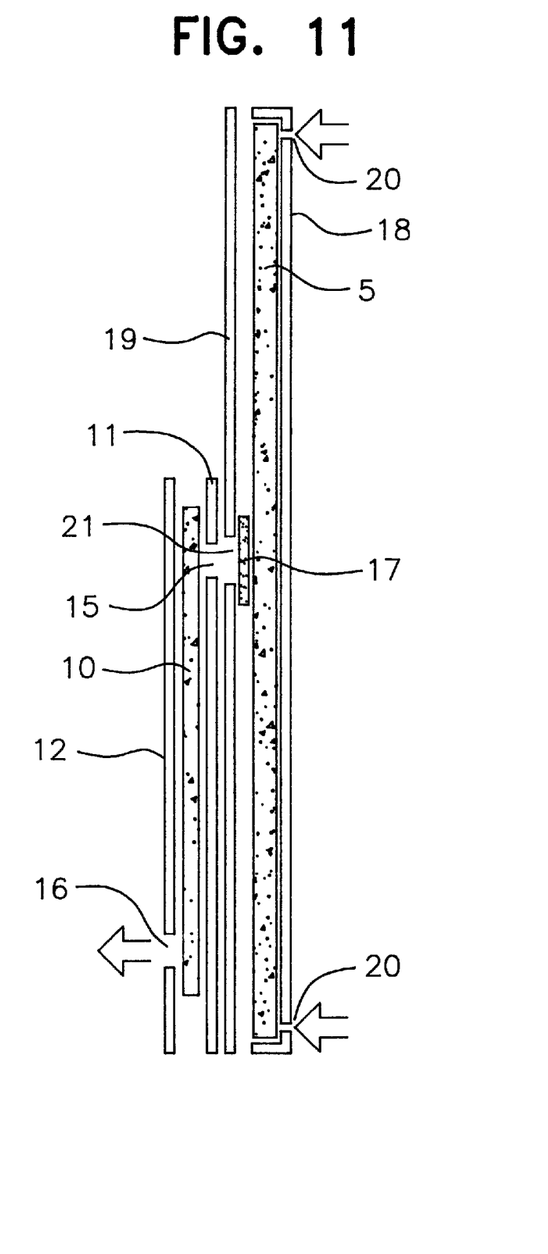
FIG. 11 shows an exploded sectional view of the embodiment of FIG. 10.

Reference is made to FIGS. 10 and 11 showing the principle of another embodiment of a filter device 9 according to the invention having a foam in the space defined by the wall 18. In this embodiment a large compartment is formed by two walls 18,19 being sealed along the edges thereof, said compartment comprising a foam material 5. In the walls are one or more openings 20 for letting in gas from the interior of the ostomy appliance. The wall 19 is secured to the wall 11 and has a hole 21 in communication with the inlet hole 15, and in this passage a hydrophobic and oleophobic membrane is placed and secured to the walls.

EXPERIMENTAL PART

EXAMPLE

Preparation of a filter part of a filter device according to the invention.

A filter body having a width of 7 mm, a length of 40 mm and a thickness of 2 mm was placed between two sandwich layers comprising four layers, EVA foil, PVDC foil, EVA binder, and a copolymer of chlorinated PE and EVA. The two layers were heat welded together, and sticked to the filter body due to the EVA layer on the foils. This new body is characterised as a "filter package".

A third foil was heat welded to the hydro and oleophobic membrane. The welded foil and membrane was welded to the filter package.

Then the filter was heat welded to the inner side of the bag.

The filter device may be used together with any ostomy appliance and may be placed inside or outside the ostomy appliance, on the front side or the back side of the appliance as it is found suitable for the application in question.

What is claimed is:

1. An ostomy appliance comprising a bag having a front wall and a rear wall of flexible material, the rear wall having an opening into the bag by which waste material can enter the bag and one of the walls having one or more vents (3) through which gas may escape from the bag and having a filter covering said vent, said filter comprising an elongated, substantially flat filter body (10) of a porous filter material interposed between gas and liquid impervious walls which are sealed to the filter body along its longitudinal side edges; gas inlet and outlet openings being provided in communication with the filter material adjacent to respective longitudinal end regions of the filter material, wherein both of the gas and liquid impervious walls are sealed to upper and lower surfaces of the filter body, the arrangement being such that in use gas flows longitudinally through the filter from the inlet opening to the outlet opening, such gas flow being confined to said filter element, wherein the inlet opening is covered by a water impermeable sheet, wherein the filter material is interposed between the gas and liquid impervious walls (11,12) forming a filter device (4) having gas inlet (15) and outlet (16) openings in communication with the filter wherein the inlet opening (15) is covered with a microporous hydrophobic and oleophobic membrane (17), the outlet opening (16) of the filter device (4) and the vent (3) are aligned, said membrane (17) is covered with a wall (18) defining a space for placing a foam material (5) between the front wall and the rear wall and covering the inlet opening of the vent and the wall (18) has one or more inlet openings (7,20) leading to the space comprising the foam material.

2. An ostomy appliance as claimed in claim 1, wherein the oleophobic membrane is sealed to the walls of the ostomy appliance around the inlet opening of the deodorising filter.

3. An ostomy appliance as claimed in claim 1, wherein the oleophobic membrane covering the inlet opening comprises a layer of a non-woven material and a layer of a PTFE-material.

4. An ostomy appliance as claimed in claim 1, wherein the foam material is hydrophobic.

5. An ostomy appliance as claimed in claim 4, wherein the foam material has been treated with a silicone oil.

6. An ostomy appliance as claimed in claim 4, wherein the foam material is oleophobic.

7. An ostomy appliance as claimed in claim 1, wherein the filter body has a curved conformation.

8. A deodorising filter device (9) for an ostomy appliance or the like, the filter comprising an elongated, substantially flat filter body (10) of a porous filter material interposed between gas and liquid impervious first and second walls which are sealed to the filter body along its longitudinal side edges; gas inlet and outlet openings in communication with the filter material adjacent to respective longitudinal end regions in the first and second walls, respectively, wherein both of the gas and liquid impervious walls are sealed to upper and lower surfaces of the filter body, the arrangement being such that in use gas flows longitudinally through the filter from the inlet opening to the outlet opening, such gas flow being confined to said filter element wherein the inlet opening is covered by a water impervious sheet, wherein the filter is interposed between the gas and liquid impervious walls (11,12) forming a filter device (4) having gas inlet (15) and outlet (16) openings in communication with the filter, the inlet opening (15) is covered with a microporous hydrophobic and oleophobic membrane (17), said membrane (17) is covered with a third wall (6,18) secured to the first wall (11) having the inlet opening (15) and defining a space wherein a foam (5) material is placed between the third wall and the first wall and covering the inlet opening of the vent and wherein the third wall has one or more inlet openings (7,20) leading to the space comprising the foam material.

9. A deodorising filter device as claimed in claim 8, wherein the oleophobic membrane is sealed to the first walls surrounding the deodorising filter.

10. A deodorising filter device as claimed in claim 8, wherein the oleophobic membrane covering the inlet opening comprises a layer of a non-woven material and a layer of a PTFE-material.

11. A deodorising filter device as claimed in claim 8, wherein the filter body has a curved conformation.

12. A filter device as claimed in claim 8, wherein the microporous oleophobic membrane is covered with a protecting layer secured to the first wall above and below the inlet of the filter.

* * * * *